United States Patent [19]

Rowles et al.

[11] Patent Number: 5,741,350
[45] Date of Patent: Apr. 21, 1998

[54] RECOVERY OF HYDROCARBONS FROM POLYALKENE PRODUCT PURGE GAS

[75] Inventors: Howard Charles Rowles, Center Valley; Lee Jarvis Howard, Allentown, both of Pa.

[73] Assignee: Air Products And Chemicals, Inc., Allentown, Pa.

[21] Appl. No.: 677,673

[22] Filed: Jul. 8, 1996

Related U.S. Application Data

[63] Continuation-in-part of Ser. No. 375,881, Jan. 20, 1995, Pat. No. 5,533,437.

[51] Int. Cl.$^6$ ............................................. B01D 53/44
[52] U.S. Cl. ............................ 95/42; 95/176; 95/177; 95/184; 95/192; 95/237
[58] Field of Search .......................... 62/606, 51.2, 617, 62/115; 95/39, 42, 172, 176, 177, 184, 192, 204, 208, 228, 237–240, 266, 288

[56] References Cited

U.S. PATENT DOCUMENTS

| | | | |
|---|---|---|---|
| 2,582,443 | 1/1952 | Linn | 95/240 X |
| 2,815,650 | 12/1957 | McIntire et al. | 95/240 X |
| 3,134,726 | 5/1964 | Hochgraf | 95/184 X |
| 3,266,221 | 8/1966 | Avery | 55/58 |
| 3,336,281 | 8/1967 | Eilbracht et al. | |
| 3,948,621 | 4/1976 | Cocuzza et al. | 95/228 X |
| 4,217,431 | 8/1980 | Zacher et al. | 526/68 |
| 4,743,282 | 5/1988 | Mehra | 95/177 X |
| 4,762,897 | 8/1988 | Asahuma et al. | 526/68 |
| 4,769,047 | 9/1988 | Dye | 55/26 |
| 5,019,143 | 5/1991 | Mehrta | 95/184 X |
| 5,233,060 | 8/1993 | Pendergast et al. | 549/523 |
| 5,376,742 | 12/1994 | Krause | 526/68 |
| 5,533,437 | 7/1996 | Howard et al. | 95/42 |

OTHER PUBLICATIONS

Fatemizadeh, A., Nolley, E., "Ethylene Recovery from Polyethylene Plant Vent Streams", American Institute of Chemical Engineers, Orlando, FL, Mar. 19–23, 1990, Paper.

Primary Examiner—Robert Spitzer
Attorney, Agent, or Firm—John M. Fernbacher

[57] ABSTRACT

Hydrocarbons are recovered from the product purge gas in an alkene polymerization process by absorption of heavier hydrocarbons from the purge gas by an intermediate hydrocarbon stream to yield a vapor rich in inert gas and alkene monomer. Alkene monomer is condensed and rectified by dephlegmation at low temperatures from the inert gas, flashed and vaporized to provide refrigeration for the condensation step, and recycled to the polymerization process. The intermediate hydrocarbon from the absorption step is recycled to the polymerization process. Optionally a portion of the inert gas is reused for purge gas.

18 Claims, 4 Drawing Sheets

RECOVERY OF HYDROCARBONS FROM POLYALKENE PRODUCT PURGE GAS

This is a continuation-in-part of U.S. Ser. No. 08/375,881, filed Jan. 20, 1995, now U.S. Pat. No. 5,533,437.

FIELD OF THE INVENTION

The invention pertains to the production of polyalkenes such as polyethylene and polypropylene, and in particular to the recovery of hydrocarbons from polyalkene product purge gas.

BACKGROUND OF THE INVENTION

In the synthesis of polyalkenes such as polyethylene and polypropylene, solid particles of polymer product are withdrawn from the reactor with interparticle gaseous components present in the reactor. The solid polymer product is purged with an inert gas such as nitrogen before the product is pelletized, yielding a nitrogen-rich purge gas containing a number of hydrocarbon compounds including unreacted ethylene or propylene, some alkanes such as ethane or propane, comonomers such as butene-1 and hexene-1, additives such as isobutane, isopentane, or isohexane which are added to the reactor feed as diluents or moderators, and small amounts of oligomers such as octene, decene, or heavier olefins. The hydrocarbon content of this product purge gas can range up to 50 mol % or higher, most of which consists of the valuable feed components ethylene or propylene. Recovery of these feed components is economically desirable, as is recovery of the comonomers and additives if present. Significant amounts of heavier components such as oligomers, if present in the purge gas, will be detrimental to adsorption or low temperature condensation methods for recovering the valuable lighter components.

Adsorption processes have been proposed to separate hydrocarbons from purge or vent gas streams produced by processes similar to polyethylene and polypropylene reactor systems. U.S. Pat. No. 3,266,221 discloses a pressure swing adsorption unit which uses molecular sieves to separate hydrocarbons, primarily ethylene and propylene, from byproduct carbon dioxide and diluent nitrogen in a direct oxidation process for the production of ethylene oxide. The recovered hydrocarbons are then compressed, purified and recycled to the reaction zone.

U.S. Pat. No. 4,769,047 discloses an improvement to that process whereby the ethylene oxide vent gas stream is first contacted with activated carbon to remove the propylene and higher hydrocarbons which have a deleterious effect when recycled to the ethylene oxide reactor with the ethylene. The ethylene is then recovered in a downstream pressure swing adsorption unit, purified by conventional liquid absorption methods to remove residual carbon dioxide, compressed and recycled to the ethylene oxide reactor system. Since heavy oligomers such as octene and decene are not formed in the ethylene oxide reactor system, there is no problem of permanent adsorption of these materials in the pressure swing adsorption units proposed in these patents. Potential problems with other heavy materials which might be present in the vent gases are not addressed in either of these patents.

Pressure-swing adsorption can be utilized to recover ethylene and propylene from the nitrogen purge gas used in polyethylene and polypropylene production processes. Most of the ethylene and propylene can be removed from the nitrogen so that a lower quantity of hydrocarbons is discharged to the atmosphere with the nitrogen. However, the purity of the recovered ethylene and propylene is too low,

2 that is, it contains too much nitrogen, to be recycled to the reactor system and instead must be burned as fuel or otherwise disposed of.

U.S. Pat. No. 3,336,281 discloses an improvement to a high pressure process for the manufacture of ethylene copolymers operating at 7350 psia or above in which ethylene off-gas from a high pressure copolymer product separator at 2940 psia or above is cooled to a temperature of 0° C. to −65° C. (+32°F. to +85°F.) by expansion to atmospheric pressure. As a result of this expansion cooling step, a large fraction of the undesirable low molecular weight by-products in the off-gas are condensed and removed and the uncondensed ethylene can be recycled to the reactor system. The improvement of this invention is directed primarily to the removal of the undesirable low molecular weight by-products from a recycle ethylene stream; the separation of ethylene from light gases such as nitrogen is not addressed. The potential problems of freeze-out of byproducts or comonomers in the cold equipment are not addressed in this patent.

U.S. Pat. No. 4,217,431 discloses an improvement to a high pressure process for the manufacture of ethylene copolymers operating at 20,000 to 75,000 psia in which off-gas from a low pressure copolymer product separator at 150 psia or less is compressed and cooled to −10° C. to −30° C. (+14° F. to −22° F.). As a result of this cooling step, a large fraction of the comonomer in the off-gas, such as vinyl acetate, is condensed and can be recycled to the reactor system. However, most of the ethylene in the off-gas, typically 60 to 70%, must be discharged from the system. The improvement of this invention is directed primarily to the recovery of the comonomer for reuse; the separation of ethylene from light gases is not addressed in the patent. The potential problems of freeze-out of byproducts or comonomers in the cold equipment are not addressed in this patent.

U.S. Pat. No. 5,233,060 discloses an absorption/stripping process to recover ethylene from argon purge gas in a direct oxidation process for the production of ethylene oxide. The ethylene is absorbed in a high molecular weight organic liquid, such as n-dodecane, and subsequently stripped from the liquid with nitrogen or methane. The stripped ethylene is then recycled to the reactor system, along with the nitrogen or methane stripping gas. Recycling of the nitrogen or methane stripping gas is acceptable in this ethylene oxide process since these gases are normally used as diluent or ballast gases in the reactor. Potential problems with accumulation of heavy materials in the scrub liquid (because these materials can only be partially stripped from the scrub liquid) are not addressed.

A paper by A. Fatemizadeh and E. Nolley presented to the American Institute of Chemical Engineers, Orlando, Fla, Mar. 19–23, 1990 entitled "Ethylene Recovery from Polyethylene Plant Vent Streams" describes in generic terms a cold box concept which uses expander refrigeration for ethylene recovery from purge gas streams containing less than 20 mole % nitrogen and other light gases. Specific details of the cold box process steps are not disclosed. A demethanizer column may be required for adequate removal of light gases. The process requires an expansion turbine and is limited to gas streams containing less than 20 mole % nitrogen. A conventional lean oil absorption process is described for recovering ethylene from such a stream in which ethylene-containing oil is regenerated and recirculated to the absorption tower.

Improved methods for the recovery of ethylene or propylene from nitrogen-rich purge gas in the production of polyethylene or polypropylene are economically desirable. The presence of heavier hydrocarbons in the purge gas can adversely affect adsorption or condensation processes used for light hydrocarbon recovery, and methods for removing such heavy hydrocarbons are needed to allow recovery of valuable ethylene or propylene. The invention disclosed below and defined in the claims which follow addresses these problems and offers improved purge gas treatment and light hydrocarbon recovery.

SUMMARY OF THE INVENTION

The invention is a method for the recovery of hydrocarbons from product purge gas (23) generated in the synthesis of a polyalkene product from a feed gas (1) comprising alkene monomer and one or more intermediate hydrocarbons in a polymerization reactor (103), wherein the product purge gas (23) is generated by purging the polyalkene product with an inert gas (21), and wherein the product purge gas (23) comprises the inert gas, unreacted alkene monomer, one or more heavy hydrocarbons formed as byproducts in the polymerization reactor, and one or more intermediate hydrocarbons having volatilities intermediate the alkene monomer and the one or more heavy hydrocarbons. The method comprises the steps of:

(a) contacting the product purge gas (23) in a gas-liquid absorption zone (117) with a scrub liquid feed (31) comprising at least one of the one or more intermediate hydrocarbons, thereby absorbing at least a portion of the one or more heavy hydrocarbons in the scrub liquid (31);

(b) withdrawing from the absorption zone (117) a vapor overhead (35) comprising the inert gas and at least a portion of the alkene monomer and an absorber bottoms scrub liquid (33) comprising at least a portion of the one or more heavy hydrocarbons;

(c) recovering the alkene monomer from the vapor overhead (35) by cooling, condensing, and rectifying the overhead in a dephlegmator system (120) to yield a hydrocarbon stream (243) rich in alkene monomer and intermediate hydrocarbons and a warmed light vapor enriched in inert gas (249); and (d) recycling at least a portion of the absorber bottoms scrub liquid (33) to the polymerization reactor (103).

The alkene monomer is ethylene or propylene, and the one or more intermediate hydrocarbons are selected from the group consisting of isobutane, isopentane, butene-1, hexane, isohexane, and hexene-1. The scrub liquid (31) comprises a hydrocarbon selected from the group consisting of isobutane, isopentane, butene-1, hexane, isohexane, and hexene-1. The one or more heavy hydrocarbons include one or more olefins having a carbon number of 8 or greater, and the inert gas preferably is nitrogen.

The product purge gas (23) may be compressed and cooled, and any condensate (27) removed therefrom, prior to treatment in the gas-liquid absorption zone (117).

At least a portion of warmed light vapor enriched in inert gas (249) can be used to supplement the inert gas 21 for purging the polyalkene product. At least a portion of the hydrocarbon stream (243) rich in alkene monomer and intermediate hydrocarbons can be utilized as scrub liquid feed (31).

In an optional mode of operation, the hydrocarbon stream (243) rich in alkene monomer and intermediate hydrocarbons is cooled in the heat exchanger (222) of the dephlegmator system (124) to yield a cooled hydrocarbon stream (261), flashed, and the resulting further cooled stream is warmed in the heat exchanger (222) to provide a portion of the refrigeration for cooling and condensing the vapor overhead (35).

An alternative embodiment of the invention comprises compressing, cooling, and partially condensing the purge vapor (23), and separating the resulting partially condensed stream (26) into a first vapor (30) rich in the inert gas which also contains portions of the unreacted alkene monomer, one or more heavy hydrocarbons formed as byproducts in the polymerization reactor, and one or more intermediate hydrocarbons having volatilities intermediate the alkene monomer and the one or more heavy hydrocarbons, and a first hydrocarbon-rich liquid (27). The alkene monomer is recovered from the first vapor (30) by cooling and condensing the overhead in a dephlegmator system (120) to yield a hydrocarbon stream (243) rich in intermediate hydrocarbons and a warmed light vapor enriched in inert gas (249).

In an optional mode of operation of this alternative embodiment, the hydrocarbon stream rich in intermediate hydrocarbons (243) is cooled in the heat exchanger (222) of the dephlegmator system (124) to yield a cooled hydrocarbon stream (261), flashing the stream, and warming the resulting flashed and cooled stream in the heat exchanger (222) to provide a portion of the refrigeration for cooling and condensing the vapor overhead (35). A warmed hydrocarbon stream (265) is withdrawn therefrom.

At least a portion of warmed light vapor enriched in inert gas (249) can be used to supplement the inert gas (21) for purging the polyalkene product. At least a portion of the warmed hydrocarbon stream (265) preferably is recycled to the polymerization reactor (103).

DETAILED DESCRIPTION OF THE INVENTION

Product purge gas from polyalkene reactors contains an inert gas such as nitrogen, the unreacted alkene monomers ethylene or propylene, hydrogen, light alkanes such as ethane or propane, and some intermediate hydrocarbons of intermediate volatility such as isobutane, isopentane, butene-1, hexane, and hexene-1. In addition, depending upon reactor system operation, the purge gas may contain varying concentrations of heavier molecular weight oligomers such as octene and decene and possibly other heavier hydrocarbons. This purge gas can be vented, utilized for fuel value or disposed of by combustion in a flare system. However, it is preferred to recover the valuable alkenes ethylene or propylene for recycle to the polymerization reactor, and optionally to recover a portion of the inert gas for reuse as high purity purge gas. Such recovery can be complicated by the presence of heavier hydrocarbons which can freeze out in low temperature processes for condensing the valuable alkenes or which can deactivate adsorbents used in adsorption processes for purification of the purge gas. The actual concentrations and phase behavior of these heavier hydrocarbons are important factors in the selection and design of purge gas treatment systems. The present invention offers several embodiments for the recovery of valuable alkenes from polymerization reactor product gas and the recovery of inert gas for reuse as high purity purge gas. The purge gas can contain light gases at concentrations between 10 and 80 mole %.

Figure 1:
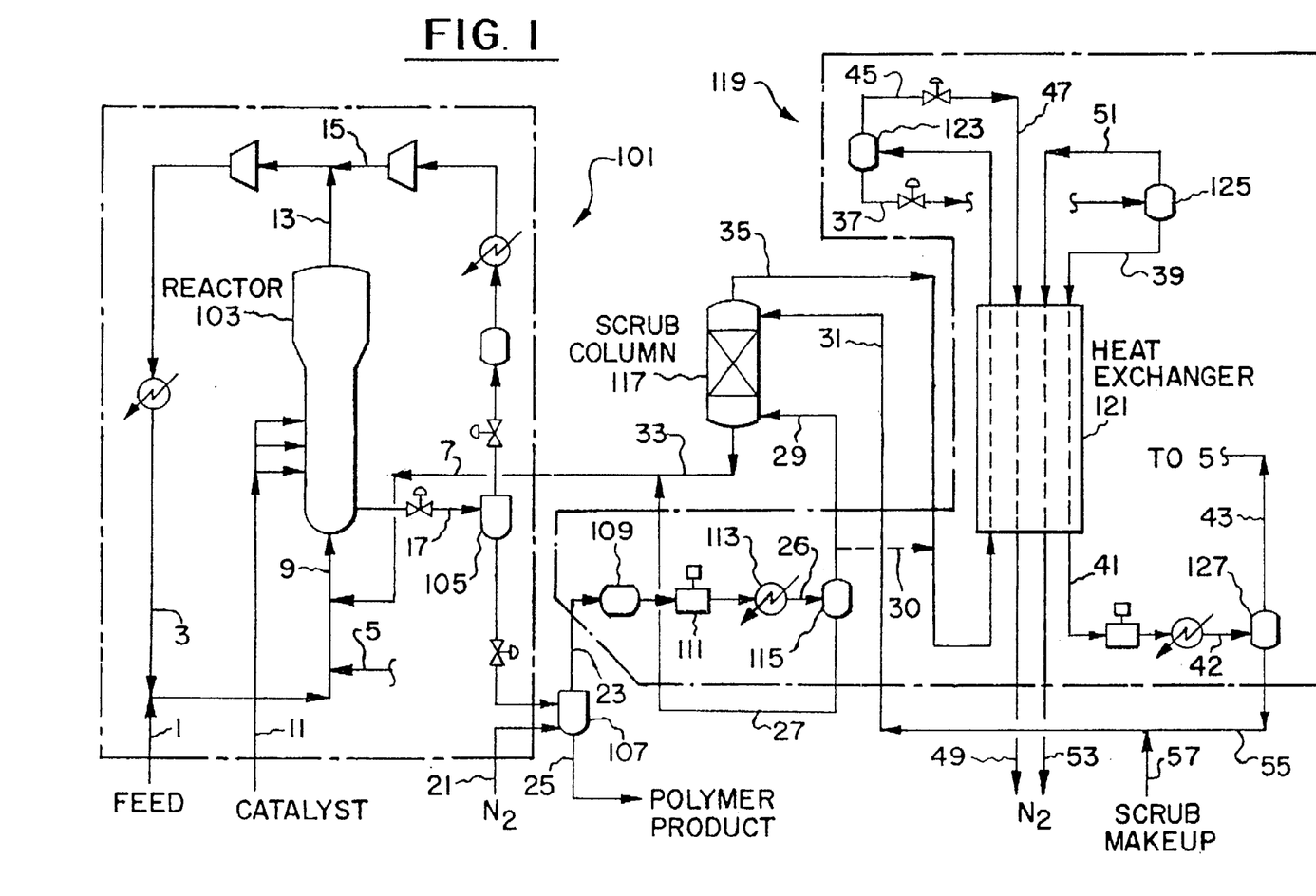
FIG. 1 is a flowsheet of an embodiment of the present invention.

The invention can be understood in detail with reference to the embodiment given in FIG. 1. Reactor system 101 for the synthesis of polyethylene or polypropylene is well known in the art and therefore will be explained only in general terms in the following description. For example, the Unipol process for polyethylene production (licensed by Union Carbide Corporation) is a widely-used gas-phase catalytic process which utilizes a fluid bed reactor at a pressure of about 300 psia. The Unipol process for the manufacture of polypropylene operates in a similar manner at a pressure of about 500 psia. In another process such as the LPE process (licensed by the Phillips Petroleum Company), ethylene and a comonomer are mixed with catalyst in an isobutane slurry and reacted in a loop reactor at about 600 psia.

In a representative polyalkene reactor operation, which in the following description is a gas-phase catalytic polyethylene reactor, feed 1 and recycle stream 3 are combined, the combined feedstream optionally is combined further with either or both of the additional recycle streams 5 and 7 (defined later), and the resulting reactor feed 9 is introduced into fluidized bed reactor 103. Catalyst 11 typically is introduced into the reactor at multiple points as shown. Unreacted gas 13 is combined with additional unreacted gas 15 and the combined stream is compressed and cooled to provide recycle stream 3. Granular polyethylene product is depressurized and withdrawn intermittently as raw product 17 which flows into separator 105. Offgas from separator 105 is cooled, compressed, and returned as stream 15 for recycle to the reactor. Granular polymer product and entrained gas flow to discharge tank 107 which is purged with nitrogen stream 21, and product purge gas 23 is withdrawn therefrom. Although nitrogen is the preferred purge gas, any inert gas can be utilized as long as it is compatible with the withdrawal and handling of the polymer product and with downstream processing of product purge gas 23. Granular polymer product 25 also is withdrawn therefrom for pelletization.

Product purge gas 23 typically contains nitrogen, a major fraction of ethylene, some hydrogen and ethane, and some intermediate hydrocarbons of intermediate volatility such as isobutane, isopentane, butene-1, hexane, isohexane, and hexene-1. In addition, depending upon reactor system operation, the purge effluent may contain heavier molecular weight oligomers such as octene and decene and possibly other heavier hydrocarbons. Typically the hydrocarbon content of product purge gas 23 is at least 20 mole % and may range up to 50 mole % or higher, most of which is valuable ethylene. This stream can be vented, flared, or used as fuel, but preferably the valuable hydrocarbons contained therein are recovered. This recovery is complicated if the earlier-mentioned oligomers and higher molecular weight hydrocarbons are present therein. To prepare product purge gas 23 for hydrocarbon recovery the stream is passed through surge vessel 109 to smooth fluctuating flow, compressed to about 200 to 700 psia by compressor 111, and cooled by cooler 113 to yield cooled purge stream 26 at about 80° to 120° F.

In one embodiment of the present invention, purge stream 26 is produced in the synthesis of polyethylene and contains primarily nitrogen, ethylene, and ethane, with smaller concentrations of isopentane (an additive to the reactor), hydrogen, and light hydrocarbons, and a small concentration of byproduct oligomers formed in the reactor. In this embodiment the oligomers and heavier hydrocarbons, which can freeze at lower temperatures, must be removed before the purge effluent is cooled to these lower temperatures to recover the ethylene. Purge stream 26, now at 200 to 700 psia and 80° to 120° F. passes into separator vessel 115 for removal of condensate 27 containing some condensed intermediate and heavier hydrocarbons. Purge vapor 29 is introduced into scrub column or gas-liquid absorption zone 117 and is contacted therein with scrub liquid 31 which absorbs the remaining heavier hydrocarbons and is withdrawn as scrub column bottoms 33. Bottoms stream 33 is combined with condensate 27 to provide recycle stream 7 which is returned to reactor 103. Nitrogen-rich overhead vapor 35 containing light components and some vaporized scrub liquid passes to recovery system 119 for recovery of valuable ethylene as well as vaporized scrub liquid components.

Scrub liquid 31 is selected to contain one or more intermediate hydrocarbons such as isobutane, isopentane, isohexane or comonomers such as butene-1, hexane, or hexene-1 which otherwise would be introduced to the reactor as an additive with feed 1. These hydrocarbons have molecular weights and volatilities intermediate the alkene monomer ethylene and the heavier oligomers and hydrocarbons mentioned earlier. In addition, the intermediate hydrocarbons used as scrub liquids should have sufficiently low freezing points that residual amounts in nitrogen-rich overhead vapor 35 will not freeze out at the low temperatures required to condense ethylene in downstream processing. Because the scrub liquid is compatible with the operation of reactor 103, scrub column bottoms stream 33 needs no additional process steps to remove absorbed heavier hydrocarbons and the entire stream can be recycled to reactor 103. Alternatively a major portion of bottoms stream 33 can be recycled to reactor 103 and the remaining portion withdrawn as a purge to prevent heavy hydrocarbon buildup in the reactor loop.

Recovery system 119 can utilize any appropriate type of separation system to remove and recover monomer and residual hydrocarbons in scrub column overhead 35. For example, refrigeration can be used to condense the monomer and residual hydrocarbons for return to the reactor system. Alternatively, the monomer and residual hydrocarbons can be removed and recovered by selective adsorption and desorption in a pressure swing adsorption process. In either case, prior removal of oligomers and heavier hydrocarbons usually is necessary to prevent buildup of these components by freezing or permanent adsorption in the downstream processing step.

In a preferred method of the present invention for recovering ethylene and residual intermediate hydrocarbons from nitrogen-rich scrub column overhead 35, the stream is cooled in one or more stages to a temperature of −150° to −225° F. and partially condensed in heat exchanger 121 against cold process streams described later and passed into separator vessel 123. The problem of heavier components freezing out in exchanger 121 does not occur because essentially all of such components were previously removed in scrub column 117. Condensed ethylene and additional light and intermediate hydrocarbons are withdrawn as stream 37 which is flashed to about 15 to 50 psia and introduced into separator vessel 125. Cold condensed liquid 39 is warmed and vaporized in exchanger 121 to provide a major portion of the refrigeration for condensation of stream 35, and the recovered vapor 41 is recompressed, cooled, and separated in separator vessel 127. Overhead vapor 43 withdrawn therefrom, containing primarily ethylene, is returned to reactor 103 as recycle stream 5 earlier described. Additional refrigeration for condensation of stream 35 is provided by Joule-Thomson (J-T) expansion of high pressure nitrogen stream 45 from separator vessel 123 and passing the cooled expanded stream 47 through exchanger 121 to yield warmed nitrogen stream 49. Optionally, a portion of warmed nitrogen stream 49 is recycled to provide purge nitrogen 21. Low pressure flashed nitrogen vapor stream 51 from separator vessel 125 is warmed in exchanger 121 to provide additional refrigeration, thus yielding warmed nitrogen stream 53 which is vented or flared. Nitrogen stream 49 typically contains 90% or more of the nitrogen in purge gas stream 26 and nitrogen stream 53 contains 10% or less of the nitrogen in purge gas stream 26.

Pressurized condensate 55, which in this case is essentially isopentane with minor amounts of other hydrocarbons, is withdrawn from separator vessel 127 at 80° to 120° F. and 200 to 700 psia, and is combined with additional scrub column makeup 57 to yield scrub column liquid feed 31 previously described. In this embodiment of the invention, isopentane is a desired additive to reactor 103 and is introduced as scrub column makeup 57 rather than with reactor feed 1.

In certain modes of operation of reactor system 101, reactor 103 may produce amounts of oligomers and heavier hydrocarbons sufficiently low such that the oligomers and heavier hydrocarbons in stream 29 will remain soluble in condensed lighter and intermediate hydrocarbon liquids 37 and 39 containing ethylene, ethane, and isopentane which condense in heat exchanger 121. The problem of heavier components freezing out in exchanger 121 therefore does not occur. In such a situation, the purge vapor stream from separator vessel 115 is taken as cooled purge stream 30 directly to heat exchanger 121 for recovery of ethylene and isopentane. Recovered hydrocarbon stream 41 from exchanger 121 is compressed and cooled to yield stream 42, which is returned directly to reactor 103 as recycle stream 5. Separator vessel 127 is not required in this case. Essentially all of the oligomers and heavier hydrocarbons in stream 30 are contained in stream 42. In this embodiment of the present invention, scrub column 117 and scrub makeup stream 57 are not required, and condensate 27 is returned directly to reactor 103 as stream 7. Optionally, purge gas stream 30 can be cooled initially in heat exchanger 121 to an intermediate temperature where most of the heavier components have condensed, for example +50° to −25° F., and then sent to an intermediate separator vessel. The condensed heavier components are separated from the uncondensed purge gas in the intermediate separator vessel and may be recovered directly. Alternatively the condensed heavier components may be rewarmed separately or may be combined with one of the other warming streams in heat exchanger 121. The uncondensed purge gas from the intermediate separator vessel is than returned to heat exchanger 121 and further cooled to condense the ethylene or propylene.

Figure 2:
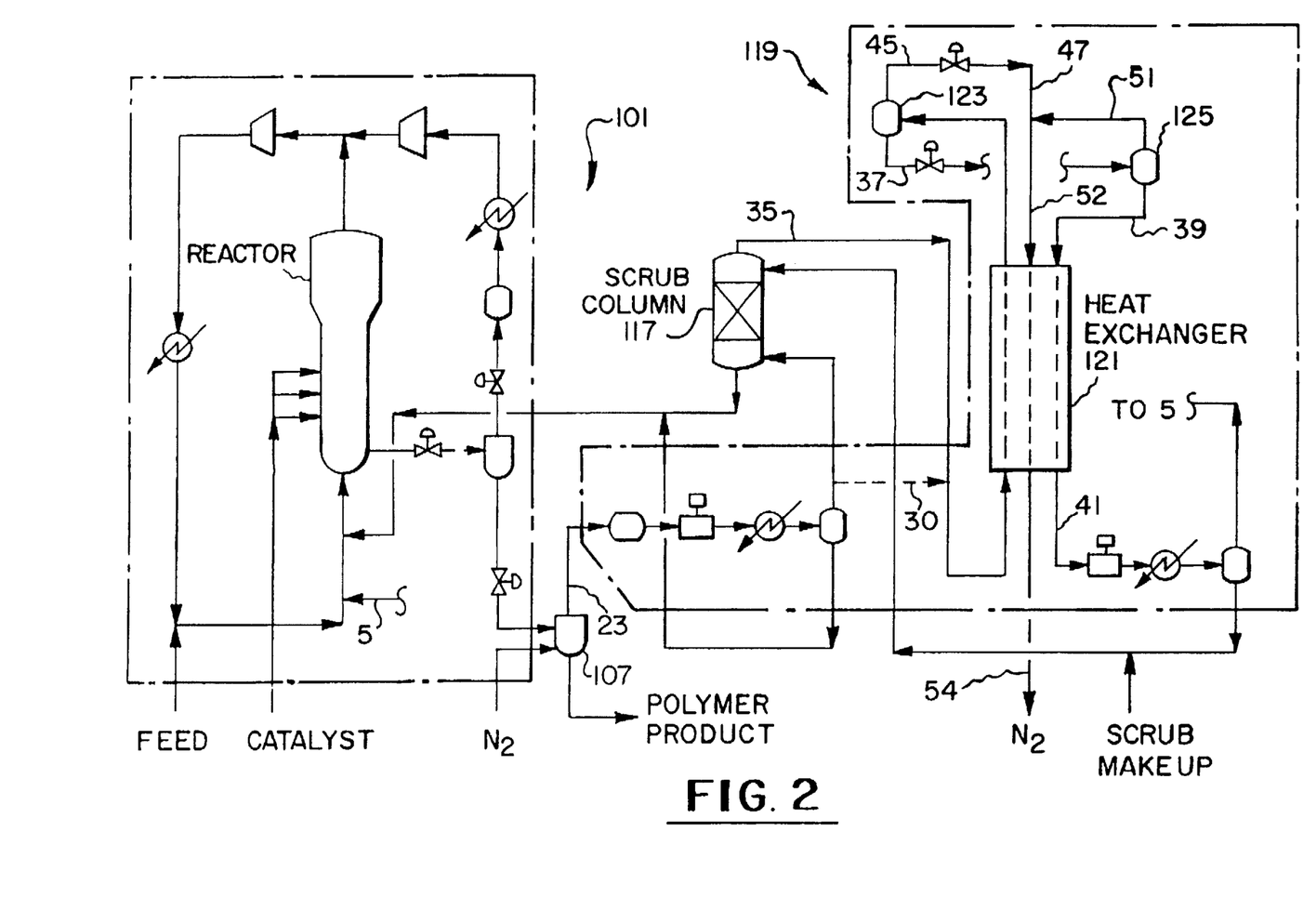
FIG. 2 is a flowsheet of an alternative embodiment of the present invention.

An alternative embodiment of the invention is illustrated in FIG. 2. Scrub column overhead 35, or optionally cooled purge stream 30 if scrub column 117 is not required, is cooled and partially condensed in heat exchanger 121 as earlier described, and the resulting stream is separated in separator 123 to yield condensate 37. Vapor 45 from separator 123 is expanded, preferably by J-T expansion across a throttling valve, to yield further cooled vapor 47; liquid 37 is flashed and separated in separator 125 to yield vapor 51 and liquid 39. In this embodiment, vapor streams 47 and 51 are combined as stream 52 which is warmed in exchanger 121 to provide additional refrigeration, and the resulting warmed nitrogen 54 is vented or flared. The amount of hydrocarbons discharged to the atmosphere if nitrogen stream 54 is vented is reduced by about two orders of magnitude compared with venting of purge gas stream 23. By combining vapor streams 47 and 51, heat exchanger 121 is simpler and operates more efficiently than in the previous embodiment; this advantage is offset by the possibility that nitrogen 54 cannot be recycled to purge vessel 107.

In another alternative embodiment, separator vessel 125 is eliminated and condensate 37, after flashing, is vaporized and warmed in heat exchanger 121. This embodiment also simplifies heat exchanger 121 but results in a higher level of nitrogen in the recovered ethylene or propylene. In another embodiment, at least a portion of the nitrogen-rich vapor 45 from separator vessel 123 is warmed in heat exchanger 121 without being reduced in pressure so that nitrogen stream 59 can be recovered at a higher pressure for purging or other uses.

Figure 3:
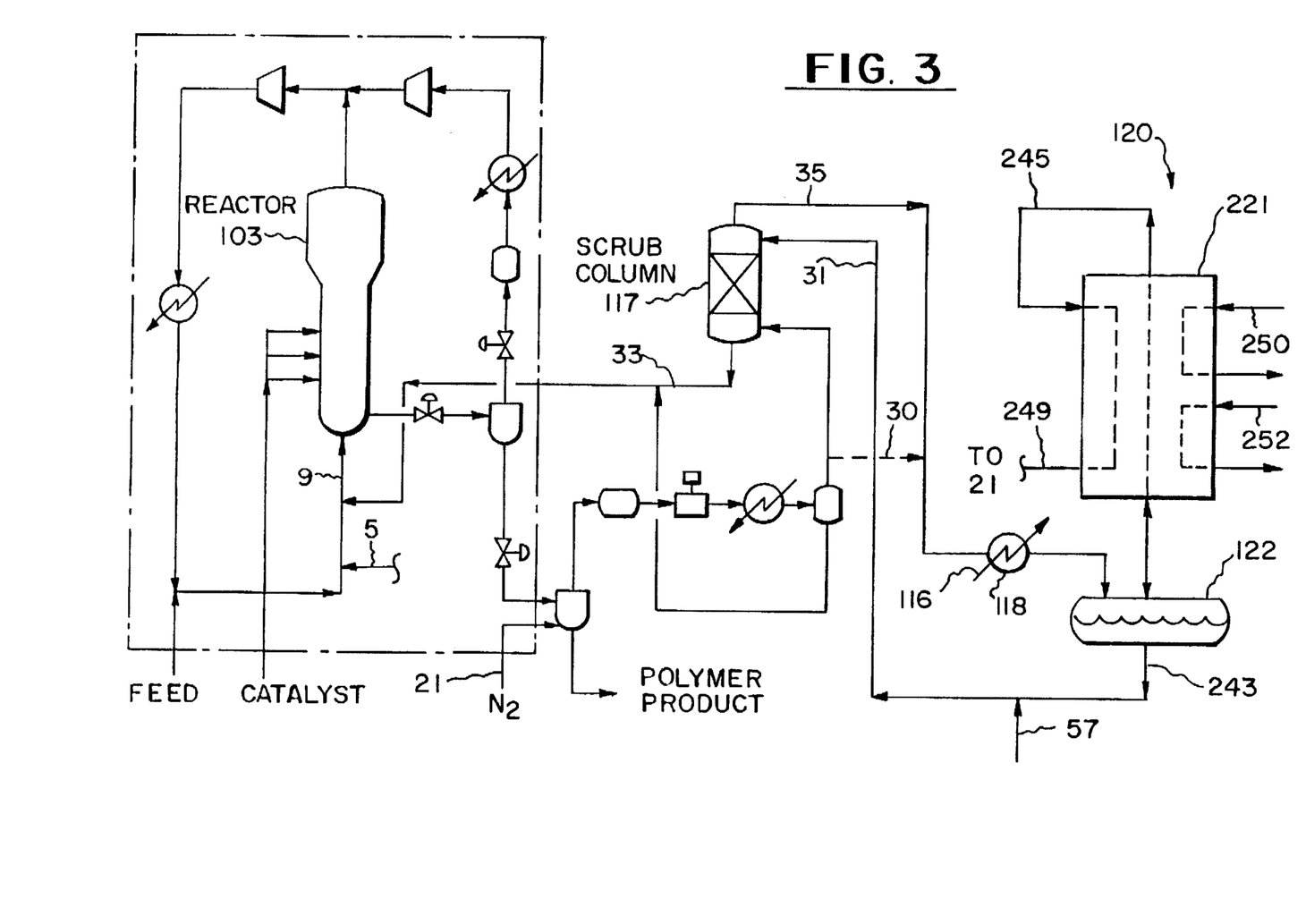
FIG. 3 is a flowsheet of another embodiment of the invention using a dephlegmator system for hydrocarbon condensation and rectification.

An alternative embodiment of the alkene monomer recovery section 119 of the invention which utilizes a dephlegmator system is illustrated in FIG. 3. Product purge gas stream 30 or 35 of FIG. 1 is preferably precooled to near the dew point of the gas using external refrigerant 116 in cooler 118. The precooled stream is introduced into separator drum 122 and is further cooled and condensed in rectifying heat exchanger 221 of dephlegmator system 120 in countercurrent flow to the descending condensed liquid to achieve a multi-stage separation. Vapor is enriched in lighter components as it rises in the dephlegmator and the liquid is enriched in heavier components as it descends in the dephlegmator. The inert and light gases are removed from the top of the dephlegmator in stream 245 and typically rewarmed to yield additional refrigeration in heat exchanger 221. Rectified hydrocarbon-rich liquid is recovered from dephlegmator system 120 via liquid collector drum 122 as stream 243 containing most of the alkene monomer and essentially all of the intermediate and heavy hydrocarbons in the purge gas. The required refrigeration for this process is typically provided by one or more external refrigerant streams 250 and 252. At least a portion of hydrocarbon-rich liquid 243 may be combined with hydrocarbon makeup 57 to provide scrub liquid 31 to scrub column 117 as earlier described. Hydrocarbon stream 33 is introduced into reactor 103 as part of feed stream 9. Warmed inert gas stream 249 optionally can be utilized to supplement polymer product purge gas 21.

Figure 4:
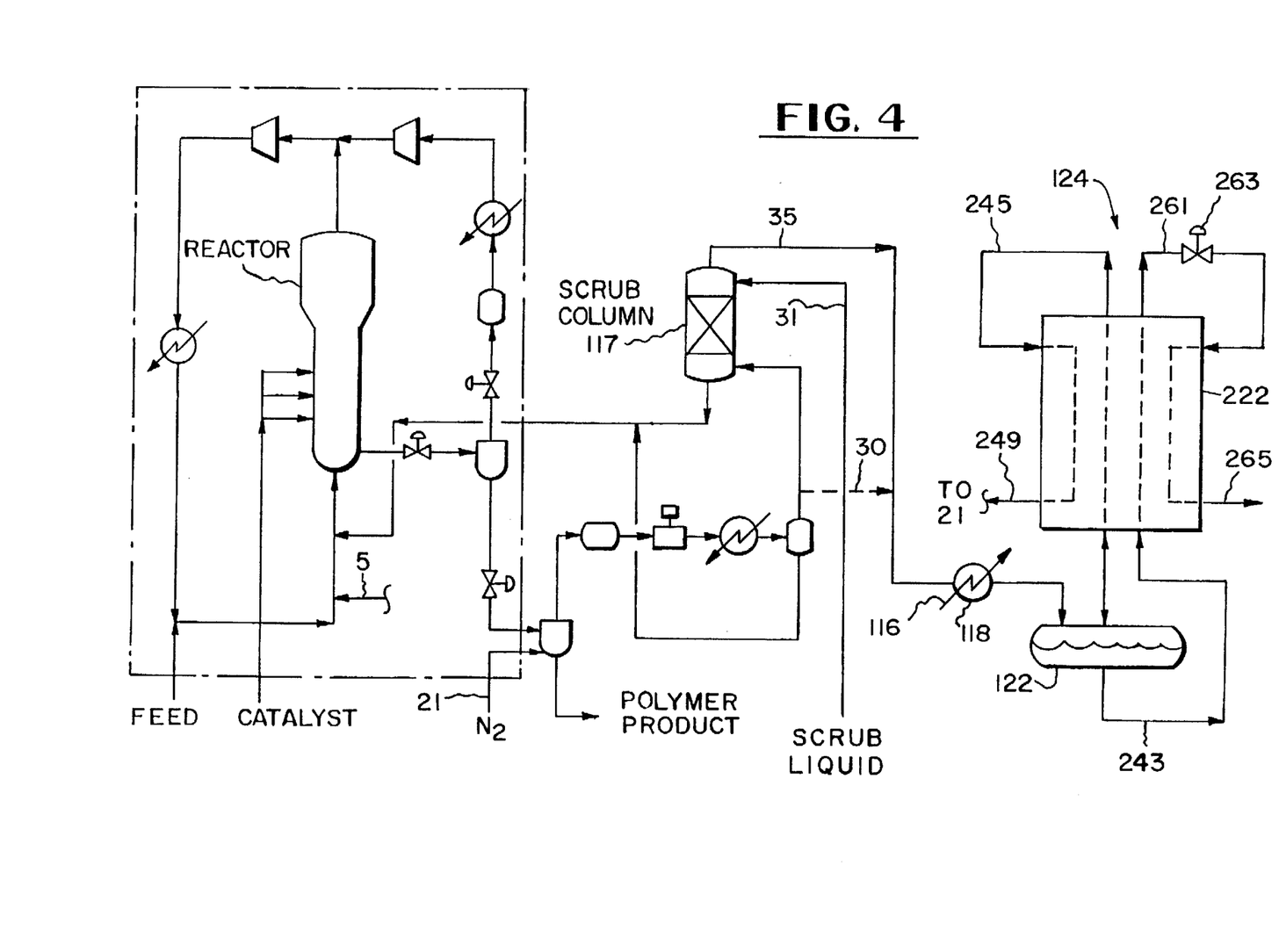
FIG. 4 is an alternative embodiment using a dephlegmator system for hydrocarbon condensation and rectification.

In an alternative embodiment illustrated in FIG. 4, rectified hydrocarbon-rich liquid stream 243 from separator drum 122 is subcooled in heat exchanger 222 of dephlegmator system 124 to yield cooled liquid stream 261, which is flashed to a lower pressure across valve 263, warmed, and at least partially vaporized in heat exchanger 222 to provide additional refrigeration for the process. In this embodiment external refrigerant streams 250 and 252 usually are not required. Warmed and vaporized hydrocarbon stream 265 can be compressed and recycled to the polymerization reactor 103. Any condensate formed during compression and cooling can be utilized for scrub column feed 31. Warmed inert gas stream 249 can be used for product purge as in the embodiment above.

In certain modes of operation of reactor system 101 as discussed earlier, reactor 103 may produce amounts of oligomers and heavier hydrocarbons sufficiently low such that the oligomers and heavier hydrocarbons in stream 29 will remain soluble in condensed lighter and intermediate hydrocarbon liquids 37 and 39 containing ethylene, ethane, and isopentane which condense in heat exchangers 221 or 222. The problem of heavier components freezing out in exchangers 221 or 222 therefore does not occur, and scrub column 117 and scrub makeup stream 57 are not required. In this case, the purge vapor stream from separator vessel 115 is taken as cooled purge stream 30 directly to cooler 118 and heat exchangers 221 or 222 for recovery of ethylene and isopentane as described above. Recovered hydrocarbon stream 243 (FIG. 3) or 265 (FIG. 4) preferably is returned directly to reactor 103 as recycle stream 5 via reactor feed 9.

To illustrate one embodiment of the invention as described above with reference to FIG. 1, a heat and material balance was carried out for treating 135 lbmoles per hour of polyethylene product purge gas 23 containing 50 mole % nitrogen, 31 mole % ethylene, 13 mole % ethane, and 4 mole % isopentane additive, with the remaining 2 mole % comprising hydrogen, other light hydrocarbons, and 5000 ppmv oligomers. Product purge gas 23 after pressure damping in surge vessel 109 is compressed to 450 psia by compressor 111, cooled to 100°F. in cooler 113, and separated in separator 115 to yield compressed vapor 29 and condensate 27 which is recycled to reactor 103 as part of stream 7. Compressed vapor 29 is contacted with 5.5 lbmoles per hour of isopentane in scrub column 117 which contains five theoretical stages of vapor-liquid contacting, and essentially all oligomers and other heavy hydrocarbons are absorbed in the scrub liquid which is withdrawn as scrub column bottoms 33. Condensate 27 and scrub column bottoms 33 are combined and recycled as stream 7 to reactor 103. The total concentration of oligomers and other heavy hydrocarbons in scrub column overhead 35 is less than 50 ppmv, which is sufficiently low that these components will not freeze out in downstream low-temperature process equipment.

Scrub column overhead 35, which is saturated with about 6 mole % isopentane, passes to recovery system 119 which in this example utilizes low temperature heat exchanger 121 to cool and partially condense overhead stream 35 as earlier described. Recovered vapor 41 from heat exchanger 121 contains 62 mole % ethylene, 25 mole % ethane, 12 mole % isopentane, and less than 1 mole % nitrogen and other light gases. Vapor 41 is compressed to 450 psia, cooled, and recovered as recycle stream 43 which contains all the ethylene and ethane and about half of the isopentane from stream 41. Stream 43 is recycled to reactor 103 as stream 5. Condensed isopentane stream 55 is combined with 1.6 lbmoles per hour of isopentane in makeup stream 57 and the combined stream 31 is returned to scrub column 117. Nitrogen stream 49, which contains about 1 mole % ethane and ethylene, optionally is recycled to provide purge nitrogen 21; otherwise the stream is vented or combusted in the plant flare system. Nitrogen stream 53, which contains higher concentrations of ethane and ethylene than stream 49, is combusted in the plant flare system.

In the alternative mode of operation of reactor system 101 discussed earlier, reactor 103 may produce very low amounts of oligomers and heavy hydrocarbons such that these oligomers and heavy hydrocarbons in stream 26 will be soluble in condensed liquids containing ethylene and intermediate hydrocarbons. This embodiment of the present invention is illustrated by the following example. Referring to FIG. 1, 100 lbmoles of product purge gas 23 withdrawn from purge vessel 107 contains 57 mole % nitrogen and 41 mole % ethylene with the remainder consisting of light hydrocarbons and hydrogen. The purge gas also contains hexene-1 comonomer and oligomers such as $C_8$ and heavier olefinic byproducts of the polymerization reaction in reactor 103. Product purge gas 23 is compressed to 400 psia and cooled to 100°F. in cooler 113. Compressed and cooled purge gas 26 is taken directly as stream 30 to heat exchanger 121 and cooled against cold process streams to −200° F. The resulting cooled and partly condensed stream is separated in separator vessel 123 into ethylene-rich liquid 37 and nitrogen-rich vapor 45 which contains less than 1.5 mole % ethylene and other hydrocarbons. Liquid 37 contains 98% of the ethylene in purge gas 30, and also contains dissolved heavy hydrocarbons such as hexene-1 and oligomers at concentrations below their respective solubility limits. Nitrogen-rich vapor 45 is reduced in pressure to 115 psia, warmed in exchanger 121 to 83° F., and vented to the atmosphere or recycled as stream 21. Ethylene-rich liquid 37 is flashed to 20 psia and passed into separator vessel 125. Dissolved nitrogen is released therein as vapor 51 from ethylene-rich liquid 39, and vapor 51 containing about 8 mole % ethylene is warmed in exchanger 121 and combusted in the plant flare. Ethylene-rich liquid 39, which contains 98 mole % ethylene and less than 1 mole % nitrogen, is vaporized and warmed to 83° F. in exchanger 121 to provide most of the refrigeration for condensation of the purge gas stream 30. Vaporized ethylene stream 41 is compressed to 400 psia and recycled to reactor 103. In this example, 97% of the ethylene in product purge gas 23 is recovered and recycled to reactor 103.

To illustrate another embodiment of the invention with reference to the alkene monomer recovery system in FIG. 3, a heat and material balance was carried out for treating 203 lbmoles per hour of purge gas stream 30 or 35 containing 86 mole % ethylene, intermediate and heavier hydrocarbons (ethylene$^+$) and 14 mole % inert and light gases (nitrogen, hydrogen, and methane) at 100° F. and 267 psia. The purge gas is cooled to −37° F., corresponding to the dew point of the purge gas, in cooler 118 using external propylene refrigerant 116 at −40° F. The purge gas is then passed via liquid collector drum 122 to rectifying heat exchanger 221 of dephlegmator system 120 where it is cooled to −117° F. to condense and rectify a hydrocarbon-rich liquid containing 97% of the ethylene and 100% of the intermediate and heavier hydrocarbons in the purge gas 30 or 35. The multiple stages of rectification achieved in dephlegmator system 120 by the counter-current vapor/liquid flow provides 173 lbmoles per hour of hydrocarbon-rich product liquid stream 243 at −38° F. and 264 psia, with 98 mole % ethylene$^+$ purity. The inert and light gases are removed from the top of the dephlegmator as stream 245, which is rewarmed for refrigeration recovery and withdrawn as stream 249 at −43° F. and 263 psia. Most of the refrigeration for the process is provided by two external ethylene refrigerant streams 250 and 252 at temperature levels of −120° F. and −96° F. respectively. Inert gas stream 249 may be used to supplement purge gas 21 if desired.

The description above and examples describe the recovery of ethylene in polyethylene production, although as earlier stated the method of the present invention alternatively can be applied to the recovery of propylene in polypropylene production. While the intermediate hydrocarbons, comonomers, and heavy hydrocarbon byproducts may be somewhat different in polypropylene production than in polyethylene production, the process steps in recovering the monomers ethylene and propylene will be the same. When low temperature heat exchanger 121 is used to recover propylene, the temperature of separator vessel 123 typically will be about −50° to −150° F. When dephlegmator system 120 is used to recover propylene, the temperature of overhead nitrogen-rich vapor stream 245 typically will be about −25° to −100° F.

Thus the embodiments of the present invention provide improved methods for recovering the light hydrocarbons ethylene or propylene from polyalkene product purge gas for recycle to the polymerization reactor. In one embodiment of the invention, oligomers and heavier hydrocarbons are removed by absorption in an intermediate hydrocarbon which is compatible with the polyalkene reactor operation. This eliminates the problems caused by freezout of the oligomers and heavier hydrocarbons when low temperature condensation is used for the recovery of light and intermediate hydrocarbons from the purge gas. This embodiment also eliminates the problem of adsorbent deactivation or permanent adsorption when adsorption-based methods are used to recover light and intermediate hydrocarbons from the purge gas. Because the intermediate hydrocarbon used for absorption is compatible with the polyalkene reactor operation, the absorption step can be operated on a once-through basis and a separate capital- and energy-intensive step for recovery of ethylene or propylene from the absorbing liquid is not required. The rich absorber bottoms liquid is recycled directly to the polymerization reactor. A distinguishing feature and advantage of the alkene condensation and recovery steps described earlier is that a large portion of the refrigeration for condensing the light and intermediate hydrocarbons can be provided through autorefrigeration by flashing and vaporizing the condensate itself before recycle as vapor to the polyalkene reactor. Additional refrigeration can be provided by J-T expansion and warming of the nitrogen-rich vapor stream(s) before recycle or flaring, so that expensive external refrigeration such as that provided by an expander is not required. Alternatively, inexpensive auxiliary refrigeration could be provided so that olefin-rich liquid stream 39 (FIG. 1) can be vaporized and recovered at higher pressures, for example above 50 psia, or as liquid product stream 243 (FIG. 3). This auxiliary refrigeration could be obtained from any convenient source such as the vaporization of liquid ethylene or propylene which is used as a feedstock in the plant or the vaporization of liquid nitrogen used as utility or purge gas in the plant. Ethylene or propylene refrigeration might be obtained from an associated ethylene plant.

The essential characteristics of the present invention are described completely in the foregoing disclosure. One skilled in the art can understand the invention and make various modifications thereto without departing from the basic spirit thereof, and without departing from the scope and equivalents of the claims which follow.

We claim:

1. A method for the recovery of hydrocarbons from product purge gas (23) generated in the synthesis of a polyalkene product from a feed gas (1) comprising alkene monomer and one or more intermediate hydrocarbons in a polymerization reactor (103), wherein said product purge gas (23) is generated by purging said polyalkene product with an inert gas (21), and wherein said product purge gas (23) comprises said inert gas, unreacted alkene monomer, one or more heavy hydrocarbons formed as byproducts in said polymerization reactor, and one or more intermediate hydrocarbons having volatilities intermediate said alkene monomer and said one or more heavy hydrocarbons, said method comprising the steps of:

(a) contacting said product purge gas (23) in a gas-liquid absorption zone (117) with a scrub liquid feed (31) comprising at least of one of said one or more intermediate hydrocarbons, thereby absorbing at least a portion of said one or more heavy hydrocarbons in said scrub liquid (31);

(b) withdrawing from said absorption zone (117) a vapor overhead (35) comprising said inert gas and at least a portion of said alkene monomer and an absorber bottoms scrub liquid (33) comprising at least a portion of said one or more heavy hydrocarbons;

(c) recovering said alkene monomer from said vapor overhead (35) by cooling, condensing, and rectifying the overhead in a dephlegmator system (120) to yield a hydrocarbon stream (243) rich in alkene monomer and intermediate hydrocarbons and a warmed light vapor enriched in inert gas (249); and (d) recycling at least a portion of said absorber bottoms scrub liquid (33) to said polymerization reactor (103).

2. The method of claim 1 wherein said alkene monomer is selected from the group consisting of ethylene and propylene.

3. The method of claim 1 wherein said one or more intermediate hydrocarbons are selected from the group consisting of isobutane, isopentane, isohexane, butene-1, hexane, and hexene-1.

4. The method of claim 3 wherein said scrub liquid (31) comprises a hydrocarbon selected from the group consisting of isobutane, isopentane, butene-1, hexane, isohexane, and hexene-1.

5. The method of claim 1 wherein said one or more heavy hydrocarbons include one or more olefins having a carbon number of 8 or greater.

6. The method of claim 1 wherein said inert gas is nitrogen.

7. The method of claim 1 which further comprises utilizing at least a portion of said warmed light vapor enriched in inert gas (249) to supplement said inert gas (21) for purging said polyalkene product.

8. The method of claim 1 which further comprises utilizing at least a portion of said hydrocarbon stream (243) rich in alkene monomer and intermediate hydrocarbons for the scrub liquid feed (31).

9. The method of claim 1 which further comprises compressing and cooling said product purge gas (23) and removing any condensate (27) therefrom prior to treatment in said gas-liquid absorption zone.

10. A method for the recovery of hydrocarbons from product purge gas (23) generated in the synthesis of a polyalkene product from a feed gas (1) comprising alkene monomer and one or more intermediate hydrocarbons in a polymerization reactor (103), wherein said product purge gas (23) is generated by purging said polyalkene product with an inert gas (21), wherein said product purge gas (23) comprises said inert gas, unreacted alkene monomer, one or more heavy hydrocarbons formed as byproducts in said polymerization reactor, and one or more intermediate hydrocarbons having volatilities intermediate said alkene monomer and said one or more heavy hydrocarbons, said method comprising the steps of:

(a) contacting said product purge gas (23) in a gas-liquid absorption zone (117) with a scrub liquid feed (31) comprising at least one of said one or more intermediate hydrocarbons, thereby absorbing at least a portion of said one or more heavy hydrocarbons in said scrub liquid (31);

(b) withdrawing from said absorption zone (117) a vapor overhead (35) comprising said inert gas and at least a portion of said alkene monomer and an absorber bottoms scrub liquid (33) comprising at least a portion of said one or more heavy hydrocarbons;

(c) recovering said alkene monomer from said vapor overhead (35) by cooling, condensing, and rectifying the overhead in a dephlegmator system (124) to yield a hydrocarbon stream (243) rich in alkene monomer and intermediate hydrocarbons and a warmed light vapor enriched in inert gas (249);

(d) cooling the hydrocarbon stream rich in intermediate hydrocarbons (243) in a heat exchanger (222) of the dephlegmator system (124) to yield a cooled hydrocarbon stream (261), flashing and further cooling the stream, and warming the resulting further cooled stream in the heat exchanger (222) to provide a portion of the refrigeration for cooling and condensing the vapor overhead (35); and (e) recycling at least a portion of said absorber bottoms scrub liquid (33) to said polymerization reactor (103).

11. The method of claim 10 which further comprises utilizing at least a portion of said warmed light vapor enriched in inert gas (249) to supplement said inert gas (21) for purging said polyalkene product.

12. The method of claim 10 which further comprises compressing and cooling said product purge gas (23) and removing any condensate (27) therefrom prior to treatment in said gas-liquid absorption zone.

13. A method for the recovery of hydrocarbons from product purge gas (23) generated in the synthesis of a polyalkene product from a feed gas (1) comprising alkene monomer and one or more intermediate hydrocarbons in a polymerization reactor (103), wherein said product purge gas (23) is generated by purging said polyalkene product with an inert gas (21), and wherein said product purge gas (23) comprises said inert gas, unreacted alkene monomer, one or more heavy hydrocarbons formed as byproducts in said polymerization reactor, and one or more intermediate hydrocarbons having volatilities intermediate said alkene monomer and said one or more heavy hydrocarbons, said method comprising the steps of:

(a) compressing, cooling, and partially condensing said product purge gas (23), and separating the resulting partially condensed stream (26) into a first vapor (30) rich in said inert gas which also contains portions of said unreacted alkene monomer, one or more heavy hydrocarbons formed as byproducts in said polymerization reactor, and one or more intermediate hydrocarbons having volatilities intermediate the alkene monomer and said one or more heavy hydrocarbons, and a first hydrocarbon-rich liquid (27); and (b) recovering said alkene monomer from said first vapor (30) by cooling, condensing, and rectifying the overhead in a dephlegmator system (120) to yield a hydrocarbon stream (243) rich in alkene monomer and intermediate hydrocarbons and a warmed light vapor enriched in inert gas (249).

14. The method of claim 13 which further comprises utilizing at least a portion of said warmed light vapor enriched in inert gas (249) to supplement said inert gas (21) for purging said polyalkene product.

15. The method of claim 13 which further comprises recycling at least a portion of the hydrocarbon stream (243) rich in intermediate hydrocarbons to the polymerization reactor (103).

16. A method for the recovery of hydrocarbons from product purge gas (23) generated in the synthesis of a polyalkene product from a feed gas (1) comprising alkene monomer and one or more intermediate hydrocarbons in a polymerization reactor (103), wherein said product purge gas (23) is generated by purging said polyalkene product with an inert gas (21), and wherein said product purge gas (23) comprises said inert gas, unreacted alkene monomer, one or more heavy hydrocarbons formed as byproducts in said polymerization reactor, and one or more intermediate hydrocarbons having volatilities intermediate said alkene monomer and said one or more heavy hydrocarbons, said method comprising the steps of:

(a) compressing, cooling, and partially condensing said product purge gas (23), and separating the resulting partially condensed stream (26) into a first vapor (30) rich in said inert gas which also contains portions of said unreacted alkene monomer, one or more heavy hydrocarbons formed as byproducts in said polymerization reactor, and one or more intermediate hydrocarbons having volatilities intermediate the alkene monomer and said one or more heavy hydrocarbons, and a first hydrocarbon-rich liquid (27);

(b) recovering said alkene monomer from said first vapor (30) by cooling, condensing, and rectifying the overhead in a dephlegmator system (124) to yield a hydrocarbon stream rich in alkene monomer and intermediate hydrocarbons (243) and a warmed light vapor enriched in inert gas (249); and (c) cooling the hydrocarbon stream rich in intermediate hydrocarbons (243) in a heat exchanger (222) of the dephlegmator system (124) to yield a cooled hydrocarbon stream (261), flashing the stream, warming the resulting flashed and further cooled stream in the heat exchanger (222) to provide a portion of the refrigeration for cooling and condensing the first vapor (30), and withdrawing therefrom a warmed hydrocarbon stream (265).

17. The method of claim 16 which further comprises utilizing at least a portion of said warmed light vapor enriched in inert gas (249) to supplement said inert gas (21) for purging said polyalkene product.

18. The method of claim 16 which further comprises recycling at least a portion of the warmed hydrocarbon stream (265) rich in intermediate hydrocarbons to the polymerization reactor (103).

\* \* \* \* \*